United States Patent [19]

Pinnavaia et al.

[11] Patent Number: 5,672,556
[45] Date of Patent: Sep. 30, 1997

[54] CRYSTALLINE SILICATE COMPOSITIONS AND METHOD OF PREPARATION

[75] Inventors: Thomas J. Pinnavaia; Peter T. Tanev, both of East Lansing, Mich.

[73] Assignee: Board of Trustees operating Michigan State University, East Lansing, Mich.

[21] Appl. No.: 527,504

[22] Filed: Sep. 13, 1995

Related U.S. Application Data

[63] Continuation of Ser. No. 293,806, Aug. 22, 1994, abandoned.

[51] Int. Cl.$^6$ .................................................. C01B 33/20
[52] U.S. Cl. ........................ 502/63; 502/159; 502/232; 423/326; 423/328.2; 423/297; 423/277
[58] Field of Search .......................... 423/700, 718, 423/328.2, 326, 277, 297; 502/63, 232, 159, 172

[56] References Cited

U.S. PATENT DOCUMENTS

| | | | |
|---|---|---|---|
| 4,665,045 | 5/1987 | Pinnavaia et al. | 502/84 |
| 5,057,296 | 10/1991 | Beck | 423/277 |
| 5,068,096 | 11/1991 | Valyocsik | 423/277 |
| 5,098,684 | 3/1992 | Kresge et al. | 423/277 |
| 5,102,643 | 4/1992 | Kresge et al. | 423/328 |

OTHER PUBLICATIONS

Meier et al., Atlas of Zeolite Structure Types Butterworth, London (1992) (no month) pp. 452, 453, 455.
Barrer et al., Zeolites, vol. 1, 130 (1981) Oct.
Lok et al., Zeolites, vol. 3, 282 (1983) Oct.
W.M. Meier and D. H. Olson, Atlas of Zeolite Structure Types, 451–543 (1992) no month.
Cartlidge, S., et al., Zeolites, 12 889–897 (1992) no month.
Zeolites 5, 349–351 (1985) no month.
Zeolites, 5, 355–358 (1985) no month.
Pinnavaira, T. J., Science, vol. 220, 365 (1983) Apr.
Martens et al., Zeolite Chemistry and Catalysis, Elsevier Sci. Publ. B.V., Amsterdam, pp. 135–143 (1991).
Davis et al., J. Am. Chem. Soc., vol. 11, 3919 (1989) (no month).
Davis et al., Nature, vol. 331, 698 (1988 no month).
Huo et al., J. Chem. Soc., Chem. Commun., 875 (1992) (no month).
Davis et al., Chem. Mater., vol. 4, 756 (1992) (no month).
Gies et al., Zeolites, vol. 12, 42 (1992) (Jan.).
Hearmon et al., Zeolites, vol. 10, 608 (1990) (Jul.).
Soghmonian et al., Angew. Chem., Int. Ed. Engl., vol. 32, 610 (1993) (no month).
Breck et al., J. Am. Chem. Soc., vol. 114, 10834 (1992) (no month).
Inagaki et al., J. Chem. Soc. Chem. Comm., vol. 8 680 (1993).
Monnier et al., Science, vol. 261, 1299 (1993) Sep.
Huo et al., Nature, vol. 368, 317 (1994) Mar.
Sing et al., Pure Appl. Chem., vol. 57, 603 (1985) (no month).
Perspectives in Molecular Sieve Science, Eds. Flank, W.H. and White T.E. Jr., ACS Symposium Series No. 368, Washington D.C., pp. 247;524;544 Jun. (1988).
Gunawardane et al., Zeolites, vol. 8 127–131 (1988) Mar.
Davis et al., XIII North American Meeting of the Catalysis Soc., Book of Abstracts, p. D14 (1993).
Sing et al., J. Am. Chem. Soc., Chem. Commun., 1257 (1993) (no month).
Cartlidge et al., Zeolites, vol. 9, 346 (1989) Jul.
Horvath, G. and K.J. Kawazoe, J. Chem. Eng. Jpn., 16, 470 (1983) (no month).
Tanev, P.T. et al., Titanium–containing mesoporous molecular sieves for catalytic oxidation of aromatic compounds, Nature vol. 368 Mar. 24, 1994.

*Primary Examiner*—Michael Lewis
*Assistant Examiner*—Stuart L. Hendrickson
*Attorney, Agent, or Firm*—Ian C. McLeod

[57] ABSTRACT

Crystalline silicate compositions having unique combinations of framework-confined uniform mesopores and textural mesopores and to a method for their preparation. The compositions typically possess a small particle size of ≦400 Å, a ratio of textural to framework-confined mesoporosity of 0.2 or greater, and a novel ability to discriminate, to adsorb, and with a metal element in the mesopores, to catalytically transform large organic molecules. The method for the formation of the mesoporous structure is accomplished by hydrogen bonding between a non-ionic amine template and a non-ionic inorganic oxide precursor followed by hydrolysis and crosslinking under mild reaction conditions. The templated products of this invention are preferably obtained using water as a hydrolyzing reagent and an alcohol as a co-solvent. The framework-confined uniform mesopore size can be expanded without the use of an auxiliary organic (pore expanding agent). The template can be easily recovered and recycled, preferably, by ethanol extraction.

23 Claims, 9 Drawing Sheets

1

CRYSTALLINE SILICATE COMPOSITIONS AND METHOD OF PREPARATION

This application is a continuation of application Ser. No. 08/293,806 filed on Aug. 22, 1994 now abandoned.

BACKGROUND OF THE INVENTION

(1) Field of the Invention

This invention relates to novel crystalline silicate compositions having unique combinations of framework-confined uniform mesopores and textural mesopores and small particle size ($\leq 400$ Å). The ratio of textural to framework mesoporosity is above about 0.2 and preferably above about 0.5. In particular, the present invention relates to such compositions formed by a novel method comprising the steps of a reaction between a neutral amine template and a neutral inorganic oxide silicate precursor, followed by further hydrolysis and crosslinking under mild reaction conditions.

(2) Description of Prior Art

Porous solids created by nature or by synthetic design have found great utility in all aspects of human activity. The pore structure of the solids is usually formed in the stages of crystallization or by subsequent treatment. Depending on their predominant pore size, the solid materials are classified as: (i) microporous, having pore size <20 Å; (ii) macroporous, with pore sizes exceeding 500 Å; and (iii) mesoporous, with intermediate pore size between 20 and 500 Å. The use of macroporous solids as adsorbents and catalysts is relatively limited due to their low surface area and relatively large non-uniform pores. Microporous and mesoporous solids, however, are widely used in adsorption, separation technology and catalysis. Owing to the need for higher accessible surface area and pore volume for efficient chemical processes, there is a growing demand for new highly stable mesoporous materials. Porous materials can be structurally amorphous, paracrystalline, or crystalline. Amorphous materials, such as silica gel or alumina gel, do not possess long range order, whereas paracrystalline solids, such as $\gamma$- or $\eta$- $Al_2O_3$ are quasiordered as evidenced by the broad peaks on their X-ray diffraction patterns. Both classes of materials exhibit a broad distribution of pores in a given product, predominantly in the mesoporous range. This broad distribution of pores limits the shape selectivity and the effectiveness of the adsorbents, ion-exchanges and catalysts prepared from amorphous and paracrystalline solids.

Another important class of porous materials is that of layered and, especially, pillared layered solids. Layered material is said to be pillared when the gallery species are sufficiently robust to prevent gallery collapse upon calcination and laterally spaced to allow for interpillar access by molecules at least as large as nitrogen (Pinnavaia, T. J., Science, vol. 220, 365 (1983)). Many naturally occurring or synthetic hosts such as layered double hydroxides, layered silicic acids, phosphates of tetravalent metals and smectite clays have been pillared (U.S. Pat. Nos. 4,458,026; 4,859,648; 4,367,163; 4,757,040). The pillaring agents usually are organic ions like quaternary ammonium ions, polycations such as $(Al_{13}O_4(OH)_{24}(H_2O)_{12})^{7+}$ or $(Zr(OH)_2(H_2O)_4)_4^{8+}$, metal oxide sols such as $TiO_2$ or $TiO_2/SiO_2$ and polyoxometalate anions such as $H_2W_{12}O_{40}^{6-}$ (U.S. Pat. Nos. 4,176,090; 4,248,739; 4,665,045 and Japanese Patent Nos. 6212611 and 6212612). The pillaring process is accomplished by swelling of the host layers followed by an ion exchange process in which the original gallery cations are substituted by the robust ions of the above pillaring agents. Often times, the pillared layered solid is calcined in order to convert the interlayer hydroxycations into stable oxide pillars. These pillared layered materials offer significant advantages over the amorphous and paracrystalline solids by allowing one to adjust the pillar and pore size, the pillar composition and the host layer charge. Moreover, their X-ray diffraction patterns are typical for well ordered materials, rather than of paracrystalline solids. However, the pore size distribution of pillared layered solids, although narrower than that of the former classes of materials, is still non-uniform. Currently, there is a considerable activity in this field, especially toward the preparation of pillared layered solids with uniform distributions of pillars and pores in the gallery.

The only class of porous materials possessing rigorously uniform pore sizes is that of zeolites and related molecular sieves. Zeolites are microporous highly crystalline aluminosilicates. Their lattice is composed by $TO_4$ tetrahedra (T=Al and Si) linked by sharing the apical oxygen atoms. Their pore network, which is confined by the spatially oriented $TO_4$ tetrahedra, consists of cavities and connecting windows of uniform size (Breck, D. W., Zeolite Molecular Sieves: Structure, Chemistry and Use; Wiley and Sons; London, (1974)). Because of their aluminosilicate composition and ability to discriminate small molecules, zeolites are considered as a subclass of molecular sieves. Molecular sieves are crystalline framework materials in which Si and/or Al tetrahedral atoms of a zeolite lattice are entirely or in part substituted by other T atoms such as B, Ga, Ge, Ti, V, Fe, or P.

Zeolite frameworks are usually negatively charged due to the replacement of $Si^{4+}$ by $Al_{3+}$. In natural zeolites this charge is compensated by alkali or alkali earth cations such as $Na^+$, $K^+$ or $Ca^{2+}$. In synthetic zeolites the charge can also be balanced by quaternary ammonium cations or protons. Depending on their Al content zeolites are classified as low silica ($1 \leq Si/Al < 2$), intermediate silica ($2 \leq Si/Al < 5$) and high silica ($Si/Al > 5$). The properties of zeolites are directly influenced by the amount of framework incorporated Al. Thus, as the Si/Al ratio increases, following the above sequence, the hydrophobicity of the framework increases and vise versa. Typical examples illustrating the relationship between Si/Al ratio and surface polarity are the hydrophilic low silica zeolite NaX, which has high affinity for water vapor, and the hydrophobic high silica Zeolite ZSM-5, which adsorbs mainly organic molecules and only small amounts of water.

Molecular sieves, such as $AlPO_4$ or $GaPO_4$ usually possess neutral framework structures due to charge compensation. Therefore, only van der Waals interactions occur between the framework and the trapped guest molecules. In contrast to the zeolites, the phosphate based molecular sieves undergo framework substitutions with difficulty. Nevertheless, Si-substituted $AlPO_4$ molecular sieves (so called SAPO's), possessing Brönsted acidity have been reported in the prior art (Jacobs et al., Zeolite Chemistry and Catalysis, Elsevier Sci. Publ. B. V., Amsterdam, p. 135, (1991)). Zeolites and molecular sieves are usually synthesized under hydrothermal conditions from aluminosilicate or phosphate gels. Their crystallization, according to the hereafter discussed prior art, is usually accomplished through prolonged reaction in an autoclave for 1 to 50 days and, often times, in the presence of structure directing agents (templates). The proper selection of template is of extreme importance for the preparation of a particular framework and pore network. A large variety of organic molecules or assemblies of organic molecules with one or more functional groups are known in the prior art to give more than 75 different molecular sieve framework structures (Meier et al., Atlas of Zeolite Structure Types, Butterworth, London (1992)). Excellent up-to-date reviews of the use of various organic templates and their corresponding structure, as well as the mechanism of structure directing are given in Barrer et al., Zeolites, vol. 1, 130 (1981); Lok et al., Zeolites, vol. 3, 282 (1983); Davis et al., Chem. Mater., Vol 4, 756 (1992); and Gies et al., Zeolites, vol. 12, 42 (1992). For example, U.S. Pat. No. 3,702,886 teaches that crystallization of aluminosilicate gel (high Si/Al ratio) in the presence of quaternary tetrapropyl ammonium hydroxide template affords zeolite ZSM-5. And primary amines such as propylamine, i-propylamine (U.S. Pat. No. 4,151,189), and diamines, such as diaminopentane, diaminohexane and diaminododecane (U.S. Pat. No. 4,108,881) also were found to direct the synthesis of the ZSM-5 type structure. However, as pointed out by Hearmon et al., Zeolites, vol. 10, 608 (1990), it is the protonated form of these amines which most likely is responsible for the framework assembly. Other publications teaching the use of various organic directing agents include, for example, U.S. Pat. No. 3,709,979, wherein quaternary cations, such as tetrabutyl ammonium or tetrabutyl phosphonium, are used to crystallize zeolite ZSM-11 and U.S. Pat. No. 4,391,785 demonstrating ZSM-12 preparation in the presence of tetraethyl ammonium cations. Another zeolite—ZSM-23 synthesis, directed by $(CH_3)_3N^+(CH_2)_7N^+(CH_3)_3$ dications, is taught in U.S. Pat. No. 4,619,820. U.S. Pat. No. 4,016,245 teaches ZSM-35 crystallization from gel solutions containing pyrrolidinium cation as template. In another example, the template of U.S. Pat. No. 4,619,820 was found to give yet another high silica zeolite—ZSM-48 (E.P.A. No. 15,132). MCM-22 and MCM-35 zeolites crystallization, taught in U.S. Pat. No. 4,981,663, mentions the use of a hexamethyleneimine template. Another U.S. Pat. No. 5,068,096 teaches that a bis(methyl pyrrolidinium) DIQUAT-4 directing agent is necessary to prepare zeolite MCM-47. The use of novel template—N,N,N,N',N',N',-hexamethyl-8,11-(4.3.3.0) dodecane diammonium diiodide, for the preparation of zeolite SSZ-26, is shown in U.S. Pat. No. 4,910,006.

As in the case of zeolites, the synthesis of molecular sieves, in particular $AlPO_4$, SAPO or $GaPO_4$, also involves the use of organic templates. For example, U.S. Pat. No. 4,310,440 teaches that tetrapropyl ammonium cations or di-n-propylamine cations afford $AlPO_4$-5 or $AlPO_4$-11, respectively. In another example, according to Davis et al., J. Am. Chem. Soc., vol. 11, 3919 (1989), tetrabutyl ammonium hydroxide was the preferred template for VPI-5 preparation. Furthermore, French Patent No. 91-03378 shows that quinuclidinium fluoride is needed to accomplish the synthesis of the large pore gallophosphate molecular sieve, cloverite.

In summary, many of the prior art molecular sieves were prepared by using quaternary ammonium cations or protonated forms of amines or diamines as templates to assemble the inorganic oxide framework.

The search for new organic directing agents, as evident in the increasing number of prior art reports, is attributable to: (i) the need for new and attractive types of stable frameworks, and (ii) to the need for expanding the uniform micropore size to mesopore region and thus allowing one to be able to adsorb, process and discriminate among much larger molecules. However, the prior art molecular sieves typically possess uniform pore size in the microporous region. This pore size is predetermined by the thermodynamically favored formation of framework windows containing 8, 10 and 12-T atom rings. Thus, the ability of the prior art zeolites and molecular sieves to adsorb, process and discriminate among molecules of certain shape and size is strictly limited by the size of these windows. During the last three decades considerable synthetic effort has been devoted to developing frameworks with pore sizes larger than that of the naturally occurring zeolite faujasite (pore size 7.4 Å). However, due to the above limitations, the synthetic faujasite analogs, zeolite X or Y, with 8 Å windows (U.S. Pat. Nos. 2,882,244 and 3,130,007), maintained for decades their position as the largest pore molecular sieves. The replacement of aluminosilicate gels by alumino- and gallophosphate gels gave new direction to the synthesis of large uniform pore materials. Thus, a 18 membered ring molecular sieve VPI-5 (Davis et al., Nature, vol. 331, 698 (1988)), was found to possess a structure with a hexagonal arrangement of one-dimensional channels (pores) of diameter ≈12 Å. The discovery of a 20-membered ring gallophosphate molecular sieve—cloverite, exhibiting a uniform pore size of 13 Å is disclosed in French Patent. No. 91-03378 (1991). Recently, Thomas et al., J. Chem. Soc., Chem. Commun., 875 (1992) reported a protonated triethyl amine cation-directed synthesis of a novel 20 membered ring aluminophosphate molecular sieve, denoted JDF-20, having uniform pore size of 14.5 Å. Very recently, a preparation of vanadium phosphate with 18.4 Å cavity was disclosed in Soghmonian et al., Angew. Chem., Int. Ed. Engl., vol. 32, 610 (1993). The exact pore size of these two materials is still to be determined. In spite of the significant progress made toward the preparation of large pore size materials, all of the above mentioned molecular sieves still possess uniform pore size in the microporous region.

A breakthrough toward the preparation of mesoporous molecular sieves have been disclosed recently in U.S. Pat. Nos. 5,098,684, 5,102,643, and 5,057,296. The claimed class of mesoporous materials (denoted as MCM-41) of this prior art was found to possess uniform and adjustable pore size in the range of 13–100 Å. Depending on preparation conditions MCM-41 type molecular sieves with hexagonal, cubic or layered crystallographic structure have been disclosed (Beck et al., J. Am. Chem. Soc., vol. 114, 10834 (1992)). The postulated mechanism of formation of these materials involves electrostatic or ion pairing interactions between quaternary ammonium liquid crystal cations, as structure directing templates, and anionic inorganic oligomer species (silicates) (U.S. Pat. No. 5,098,684). Related mesoporous structures also have been prepared by rearrangement of a layered silicate (kanemite) (Inagaki et al., J. Chem. Soc. Chem. Comm., vol. 8, 680 (1993)) in the presence of quaternary ammonium cations. The mechanism of formation of MCM-41 type materials has been recently refined by Monnier et al., Science, vol. 261, 1299 (1993). According to this mechanism, the preparation of hexagonal mesoporous silica is accomplished through the initial formation of a lamellar phase of $SiO_2$ oligomers. These $SiO_2$ anionic species act like multidentate ligands with high charge density and drive the cationic quaternary ammonium surfactant toward an assembly of hexagonal rod-like micelles with the positive charge concentrated on the micelle surface. Thus, the final formation of the hexagonal MCM-41 phase was attributed to strong electrostatic interactions (ion pairing) between the positively charged micelles and the anionic silicate. More recently, Huo et al., Nature, vol. 368, 317 (1994), proposed four possible pathways to the synthesis of template-inorganic biphase arrays. Pathway 1 involves the direct co-condensation of anionic inorganic species with cationic template ($S^+T^-$); the synthesis of prior art MCM-41 materials is prototypic example (U.S. Pat. No. 5,098,684). A similar approach was taken in a charge reversed situation (pathway 2) where an anionic template was used to direct the condensation of cationic inorganic oxide species ($S^-I^+$). The pathway 2 has been found, by Huo et al., Nature, 368, 317 (1994), to give a hexagonal iron and lead oxide and different lamellar lead and aluminum oxide phases. By contrast the proposed pathways 3 and 4 involve condensation of ionic inorganic species mediated by counteranions of opposite charge to that of the template head group (solution species ($S^+X^{31}\;I^-$) where $X^{31}=Cl^{31}$, $Br^{31}$; or, ($S^-M^+I^-$) where $M^+=Na^+$, $K^+$). It has been found that prior art hexagonal MCM-41 or cubic or even lamellar phase can also be prepared by pathway 3 mechanism using quaternary ammonium cations and strongly acidic conditions (1–7M HCl or HBr). In another example, a condensation of anionic aluminate species was accomplished by alkali cation mediated ($Na^+$, $K^+$) ion pairing with an anionic template ($C_{12}H_{25}OPO_3^-$). The preparation of the corresponding Al(OH)$_3$ lamellar phase in this case has been attributed to the fourth pathway ($S^-M^+I^-$). Nevertheless, the mechanism of formation of these structures is still based on charge matching and ion pairing between ionic organic directing agent and ionic inorganic gel. The limitations of this approach are that the quaternary ammonium cation template is very expensive, toxic and difficult to recover. According to U.S. Pat. No. 5,098,684 the quaternary ammonium cation template is not recovered but burned off from the templated product by calcination at temperatures above 500° C.

Hereafter, we define and differentiate the terms framework-confined uniform porosity and textural porosity. Framework-confined uniform pores are pores formed by nucleation and crystallization of the framework elementary particles. These pores typically are intersecting cavities and channels defined by the solid framework. The size of the cavities and channels, i.e. the size of the framework-confined uniform pores, in molecular sieve materials is highly regular and predetermined by the thermodynamically favored sizes of the windows. The framework-confined pores of freshly crystallized product are usually occupied by the template cations and water molecules. While water molecules are easily removed by heating and evacuation, the quaternary ammonium cations, due to their high charge density, are strongly bound or confined to the pore cavities and channels of the negatively charged framework. Therefore, they are difficult to remove from the structure of the prior art molecular sieves. Textural porosity is the porosity that can be attributed to voids and channels between elementary particles or aggregates of such particles (grains). Each of these elementary particles in the case of molecular sieves is composed of many framework-confined uniform pores. The textural porosity is usually formed in the stages of crystal growth and segregation or subsequent thermal treatment or by acid leaching. The size of the textural pores is determined by the shape, size and the number of particle contacts of these particles or aggregates. Thus, the size of the textural pores is usually at least one or two orders of magnitude larger than that of the framework-confined pores. For example, the smaller the particle size, the larger the number of particle contacts, the smaller the textural pore size and the larger the surface area of these textural pores. One skilled in the art of transmission electron spectroscopy (TEM) could determine the existence of framework-confined micropores from High Resolution TEM (HRTEM) images or that of framework-confined mesopores from TEM images obtained by observing microtomed thin sections of the material as taught in U.S. Pat. No. 5,102,643. In addition, one skilled in the art of adsorption could easily distinguish and evaluate framework-confined uniform micropores by their specific adsorption behavior. Such materials usually give a Langmuir type (Type I) adsorption isotherm without a hysteresis loop (Sing et al., Pure Appl. Chem., vol. 57, 603 (1985)). The existence of textural mesoporosity can easily be determined by one skilled in the art of SEM, TEM and adsorption. The particle shape and size can readily be established by SEM and TEM and preliminary information concerning textural porosity can also be derived. The most convenient way to detect and assess textural mesoporosity is to analyze the $N_2$ or $Ar_2$ adsorption-desorption isotherm of the solid material. Thus, the existence of textural mesoporosity is usually evidenced by the presence of a Type IV adsorption-desorption isotherm exhibiting well defined hysteresis loop in the region of relative pressures Pi/Po>0.4 (Sing et al., Pure Appl. Chem. vol. 57, 603 (1985)). This type of adsorption behavior is quite common for a large variety of paracrystalline materials and pillared layered solids.

The microporous zeolites and molecular sieves of the prior art exhibit mainly framework-confined uniform micropores, and no textural mesoporosity as evidenced by their Langmuir type adsorption isotherms without hysteresis loops at Pi/Po>0.4 and the large crystalline aggregate size of >2 μm, more usually from 5 to 20 μm. The typical values for their specific surface area are from 300–800 m$^2$/g and for the total pore volume $\leq 0.6$ cm$^3$/g (Perspectives in Molecular Sieve Science, Eds. Flank, W. H. and White T. E. Jr., ACS symposium series No. 368, Washington D.C., p. 247; 524; 544 (1988)). Most of these structures are prepared by prolonged crystallization at hydrothermal conditions, using quaternary ammonium cations or protonated primary, secondary or tertiary amines to assemble the anionic inorganic species into a framework. It should also be noted that the use in the prior art of non-ionic amines and alcohols as templates (Gunawardane et al., Zeolites, vol. 8, 127 (1988)) has led to the preparation of only microporous highly crystalline (particle size>2 μm) molecular sieves that lack appreciable textural mesoporosity. For the mesoporous molecular sieves of the MCM-41 family the uniform mesopores are also framework-confined. This has been verified by TEM lattice images of MCM-41 shown in U.S. Pat. No. 5,102,643. Therefore, the framework of this class of materials can be viewed as an expanded version of a hexagonal microporous framework. The existence of these framework-confined uniform mesopores was also confirmed by the capillary condensation phenomenon observed in their adsorption isotherms. Typical $N_2$ adsorption-desorption isotherm of MCM-41 (Davis et al., XIII North American Meeting of the Catalysis Soc., Book of Abstracts, p. D14 (1993)) is included here for reference (FIG. 1). This adsorption isotherm is essentially the same as that obtained previously by Sing et al., J. Am. Chem. Soc., Chem. Commun., 1257 (1993). The isotherm is constituted by sharp adsorption uptake followed by a hysteresis loop in the Pi/Po region of 0.3 to 0.4. This hysteresis corresponds to capillary condensation into the framework-confined uniform mesopores. The lack of appreciable hysteresis beyond Pi/Po>0.4 implies the absence of textural mesoporosity. This lack of textural mesoporosity is also supported in some cases by the highly ordered hexagonal prismatic shaped aggregates of size >2 m (Beck et al., J. Am. Chem. Soc., vol. 114 10834 (1992)). The total pore volume of the material reported by Davis et al is $\approx 0.7$ cm$^3$/g and that of the framework-confined mesopores, as determined from the upper inflection point of that hysteresis loop, is almost equal to that of the total pore volume.

Therefore, the ratio of textural to framework-confined mesoporosity here approaches zero. The size of the framework-confined uniform mesopores is ≈30 Å. Another prior art reference, U.S. Pat. No. 5,098,684, teaches that the size of these framework-confined uniform mesopores can be varied by varying the size of the template alkyl chain. However, the use of quaternary ammonium templates with alkyl chains from 6 to 16 carbon atoms seems to give relatively small variations in the uniform pore size—from 20 to 40 Å. The most preferred template of this prior art—cetyltrimethyl ammonium hydroxide gave pores of size ≈35 Å.

A method to further expand the framework-confined uniform mesopore size of MCM-41 is taught in the recent patent, U.S. Pat. No. 5,057,296. According to this method the pore size is expanded by adding auxiliary organic to the initial gel/surfactant mixture. This auxiliary organic typically is an aromatic or cyclic aliphatic compound of from 6 to 20 carbon atoms. However, according to this prior art, the uniform pore size was expanded to up to ≈70 Å, but beyond this value a material with non-uniform pore distribution from 70-120 Å was obtained. It is obvious that crystalline uniform pore materials of the aforementioned prior art typically lack appreciable textural mesoporosity. However, there is increasing number of reports in the literature suggesting that textural mesopores behave as transport pores to the framework-confined uniform pores and that they greatly improve the access and the performance of adsorbents, ion-exchangers and catalysts. This, for example, is demonstrated in Ger. Pat. (DD) No. 289,419 and in Cartlidge et al., Zeolites, vol. 9, 346 (1989) which teach the leaching of Al containing mordenite and US-CSZ-1, respectively. According to this prior art the leaching process generates a "swiss-cheese" like transport pore network, consisting of textural mesopores, which greatly improves the overall catalytic performance. That is, the transport pores provide more efficient assess to the framework-confined micropores of the zeolite. Two features are characteristic of this prior art: (i) the uniform framework-confined mesopores can be expanded up to ≈70 Å by adding auxiliary organic, but this adds to the expense of the preparation art, and (ii) the attempts to expand the uniform framework-confined mesopores beyond the 70 Å limit fail, giving materials with non-uniform pore size distribution. In conclusion, these prior art preparation approaches do not generate the desired molecular sieve materials with comparable framework-confined uniform mesoporosity and textural mesoporosity. Thus, one can anticipate that the accessibility of the framework-confined uniform mesopores of prior art materials will be low and that large amounts of side products can be expected in catalytic reactions performed by these MCM-41 type materials with expanded pore size >70 Å. Consequently, the prior art molecular sieve materials, as well as their preparation method have the following disadvantages:

1. The absence of an optimal balance of framework-confined and textural mesoporosity. This deficiency is attributable in part to the specific preparation conditions of the prior art molecular sieves which afford materials with relatively large particle size. The particle size of the prior art materials is typically >2 μm. This does not contribute to improving the textural mesoporosity and to accessing to the framework-confined uniform mesopores. The lack of textural mesoporosity could lead to serious diffusion limitations in many potential applications. The ratio of textural to the framework-confined mesoporosity of these materials is usually close to zero.

2. The prior art method uses quaternary ammonium cations as templates that are very expensive, very difficult to recover and highly toxic and, therefore, potential health hazards. In all the prior art examples the templates were simply burned off in order to access the pore network. The prior art also used protonated and non-protonated primary amines, diamines or alcohols as templates, to assemble a variety of molecular sieve frameworks, but these templates afforded only uniform framework-confined microporous materials, with little or no complementary textural mesoporosity. The use of auxiliary organic in the prior art expands the framework-confined uniform mesopores to certain limit (≈70 Å), but these auxiliary reagents do not generate the desired complementary textural mesoporosity. Also, the use of auxiliary organics makes the prior preparation art even more expensive. Another disadvantage of the prior art is that it utilizes prolonged hydrothermal reactions that are carried out in an autoclave at temperatures from 120° to 200° C. for 1 to 50 days to prepare the crystalline products.

All of the aforementioned disadvantages of this prior art severely limit the practical use of these crystalline materials.

Therefore, there is a need for new, templated, silicate structures with complementary framework-confined uniform mesoporosity and textural mesoporosity and for a new effective art which would allow cost reduction by employing less expensive reagents, mild reaction conditions. Most importantly there is a need for an art which would provide templated synthesis of framework-confined and textural mesopores but also allow for the effective recovery and recyclability of the template.

OBJECTS

An object of the present invention is to provide a new approach to the design of crystalline, silicate compositions containing balanced uniform framework-confined mesoporosity and textural mesoporosity and small particle size ≦400 Å, while at the same time providing for facile recovery of the template.

Another object of the present invention is to provide mild reaction conditions for preparation of the composition of this invention.

Still another object of this invention is to provide for the facile recovery and recycling of the template by new separation art involving extraction or vacuum distillation from the crystalline product.

Yet another object of the present invention is to provide inexpensive preparation methods for these materials by avoiding the use of expensive quaternary templates and high temperature hydrothermal synthesis conditions.

Yet another object of the invention is to provide an inexpensive means of expanding the framework-confined uniform mesopore size of these compositions circumventing the use of auxiliary organic (pore expansion agent).

Still another object of the present invention is to provide applications of these materials as adsorbents, catalysts and catalytic supports.

These and other objects will become increasingly apparent from the following description and the drawings.

SUMMARY OF THE INVENTION

Figure 1:
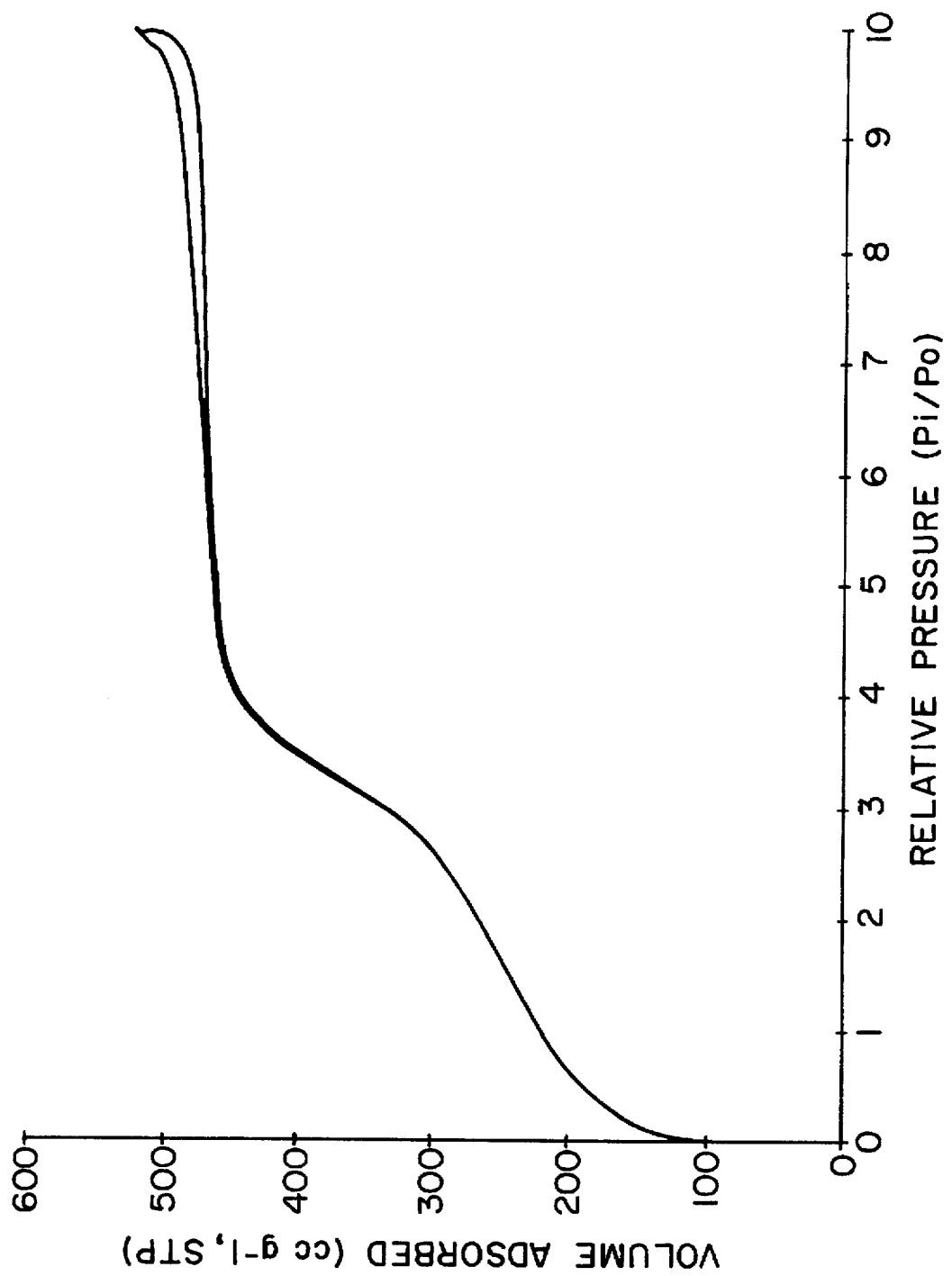
FIG. 1 is a representative $N_2$ adsorption-desorption isotherm for the MCM-41 product from Davis et al., XIII North American Meeting of the Catalysis Soc., Book of Abstracts, p. D14 (1993).

The present invention relates to a crystalline silicate composition having uniform framework confined mesopores and textural mesopores with a particle size of less than about 400 Å, two hysteresis loops in a N₂ adsorption-desorption isotherm, a ratio of textural to framework mesopores of at least about 0.2 and a specific surface area of 300 to 1500 square meters per gram.

The present invention particularly relates to a crystalline silicate composition having uniform framework-confined mesopores and textural mesopores prepared by a method which comprises reacting a neutral silicon containing precursors and a neutral amine template to form a reaction product, hydrolysis of the reaction product with an aqueous solution and removal of the template and the aqueous solution.

The present invention also relates to a method for preparation of a synthetic, crystalline silicate composition comprising: preparing an aged, non-ionic silicon or silicon substituted precursor solution with stirring at a temperature of at least 0° C. for at least 5 minutes (aging is optional); preparing a homogeneous solution of a non-ionic amine template in a hydrolysis agent and co-solvent (optional) with stirring at a temperature between about 0° and 100° C.; mixing of the solutions of steps (a) and (b) at a temperature between about 0° and 100° C. to form a gel which is aged for at least thirty minutes to form a crystalline product; separating the template and at least some of the hydrolysis agent from the crystalline product; and optionally calcining the crystalline product at 300° to 1000° C. for at least about 30 minutes.

The present invention provides a new class of silica-based crystalline materials with complementary framework-confined uniform and textural mesopores and typically small particle size and that can be used as an adsorbents and catalysts for the catalytic conversion of organic substrates. This new class of materials is distinguished from these by the prior art by possessing significant amount of textural mesoporosity, typically very small particle size <400 Å and a ratio of textural to framework-confined mesoporosity typically ≧0.2.

In addition, the crystalline silicate compositions of the present invention are obtained by the new preparative method. According to the method of the present invention, the formation of the mesoporous structures is believed to be accomplished primarily by H-bonding between neutral silicon precursors and a neutral amine template, followed by further hydrolysis and crosslinking of TO₄ units under mild reaction conditions. This H-bonding most likely occurs between a surface silanol groups (Si—OH) or, more generally, any T—OH or T-proton donor compound, and the lone pair of electrons on the N atom of the organic amine template. Specifically, the said method comprises formation of a gel by mixing of a non-ionic template solution with a clear aqueous solution of silicon or silicon substituted alkoxide in the presence of a hydrolysis agent and a co-solvent (optional), followed by aging and crystallization under stirring at temperature of at least 0° C. for at least 0.5 h. Much of the template can be recovered by extraction of the templated product with hot water or with ethyl alcohol, or a mixture thereof, or other solvents or by vacuum distillation, more preferably by extraction with alcohol. Complete removal of the last traces of template and the further crosslinking of the TO₄ framework is accomplished by calcination at 300° to 1000° C.

Applicants are unaware of prior art teaching the present crystalline compositions of silicate-based molecular sieve material having complementary framework-confined uniform mesoporosity and textural mesoporosity and small particle size (≦400 Å). Also, Applicants know of no prior art teaching the preparation of these compositions by H-bonding between non-ionic amine template and non-ionic silicon precursor, hydrolysis and crystallization under mild reaction conditions and template recovery and recycling by extraction or distillation of the templated product.

This result is achieved by using the neutral amine templates to assemble neutral reactant precursors into a mesoporous framework structure, while at the same time limiting crystal growth in most cases to a range where complementary textural mesoporosity is achieved. Hydrogen bonding between the template and the reagent is believed to be the primary driving force of the framework assembly process of this invention. Here the non-ionic or neutral amine plays the role of both a solvent and template for the non-ionic precursor. Water plays a role as a hydrolysis reagent and the alcohol solvent acts as co-solvent.

The molar ratio of amine to SiO₂ in the as synthesized crystalline composition is between about 0.05 and 1, preferably 0.27. The crystalline silicate composition of the present invention preferably has in its calcined and anhydrous state the following formula:

$$K_xM_ySi_zO_q$$

wherein K is optional and is at least one trivalent element selected from the group consisting of B, Al, Ga, Cr or Fe; M is optional and is at least a tetravalent element selected from the group consisting of Ti, V, Ge or Zr; Si is silicon, O is oxygen and x, y, z and q are the molar parts of K, M, N and O, respectively. One skilled in the art can also substitute Si completely for Ge. In the calcined composition x is between 0.001 and 0.5; y is between 0.001 and 0.4; z is between 0.4 and 1 and q is between about 1 and 3. Preferably y is between about 0.005 and 0.25. Preferably q is 2.

The crystalline mesoporous material of this invention may be characterized as formed by H-bonding between neutral inorganic oxide precursors containing TOH groups as hydrogen donors and neutral amine templates as hydrogen acceptors, followed by further hydrolysis and crosslinking of TO₄ units under mild reaction conditions. This H-bonding most likely occurs between a surface silanol group (Si—OH) or more generally any T—OH or T-proton donor compound in which the T metal is tetrahedrally coordinated to four oxygens and the lone pair of electrons on the N atom of the organic template. Specifically, the method comprises formation of a gel by mixing of a non-ionic template solution with a clear solution of silicon or silicon-substituted alkoxide in the presence or in the absence of a co-solvent, followed by hydrolysis, aging and crystallization under stirring at a temperature of at least 0° C. for at least 0.5 hours. More particularly, the calcined composition of this invention is characterized by one strong X-ray diffraction peak at a d-spacing greater than 20 Å and diffuse scattering at ≈15±3 Å. The said compositions are distinguished in part from prior art MCM-41 materials by the very small particle size <400 Å. More specifically, the crystalline composition of this invention may be distinguished from those of prior art, including MCM-41 materials, by the presence of complementary textural mesoporosity. A distinctive feature of the preset composition is that the ratio of textural to framework-confined mesoporosity can be varied in the range from 0.2 to 10 by careful selection of the membrane amine template and the reaction conditions. Thus, by varying the textural to framework-confined mesoporosity ratio one can mediate the accessibility of the pore structure of the crystalline product, depending on the demands of the particular application. The said compositions can be used as an adsorbent or a catalyst, providing the neutral amine template has been removed. According to this invention the removal of the template from the reaction product can be achieved by at least three ways; (i) air drying following by calcination in air or in inert gas at temperatures from 300°–1000° C. for 30 minutes to 72 hours; (ii) washing of the wet product with hot water or/and alcohol; and (iii) by vacuum evaporation from the air dried product. The fact that the template can be recycled by recovery methods (ii) and (iii) is also a distinctive feature of this invention. Procedure (i) results in the destruction of the template. The separation of the template by washing or distillation is preferably followed by air drying and calcination in air or inert gas to remove the final traces of template and to complete the crosslinking of the mesostructure.

The products of the present invention have a specific surface are ($S_{BET}$) of between 300 and 1500 m²/g. The specific surface area was calculated using the formula:

$$S_{BET} = V_m N_a a_m$$

where:

$V_m$—the volume of $N_z$ adsorbate for monolayer surface coverage.

N—Avogadro's number.

$a_m$—cross-sectional area of the adsorbate molecule (assumed to be 16.2 Å² for $N_2$).

The $V_m$ is obtained from the linear part of the Brunauer-Emmett-Teller equation (Brunauer's et al J. Am. Chem. Soc., 60, 309 (1938)). This equation in its most common form is given by:

$$\frac{Pi}{V_a(Po - Pi)} = \frac{1}{V_m C} + \frac{C-1}{V_m C} \times \frac{Pi}{Po}$$

where $V_a$—volume of $N_2$ adsorbed at given Pi/Po.

C—the so-called BET constant, which is related to the enthalpy of adsorption.

Pi—the equilibrium pressure of $N_2$ adsorbate.

Po—the saturation pressure of the adsorbate at −195° C.

After template removal and calcination, the said material can be used as an adsorbent for non-polar or polar organic molecules or as a gas drying agent. Furthermore, the said calcined product when framework substituted, or subsequently impregnated, as taught in Ger. Pat. (DD) No. 286, 522, with proper amount of catalytically active element, such as Al, Ti, V, Pt, Pd, Cu, Cr or mixture thereof, or when treated with transition metal macrocycles, could be used as a catalyst for cracking, hydrocracking, hydrogenation-dehydrogenation, isomerization or redox reactions involving organic substrates.

The method for the preparation of the compositions of this invention involves the preparation of clear solutions comprising sources of tri- or tetravalent elements, or mixture thereof, a source of silica and solvent, aging and reacting this solution with template solution at mild reaction conditions, under stirring, until formation of the desired crystalline product and recovering the crystalline material. The said template can be described more particularly as a neutral (non-ionic) molecule of formula $R_1R_2R_3N$, wherein N is nitrogen and at least one of $R_1$, $R_2$ and $R_3$ is selected from the group of alkyl of from 6 to 18 carbon atoms or aryl of from 6 to 18 carbon atoms or combination thereof. The remaining groups of $R_1$, and $R_3$ are selected from the group consisting of hydrogen or alkyl from 1 to 18 carbon atoms or combination thereof. In addition, said material successfully can be synthesized in the presence of neutral diamines of formula $R_4R_5N$—X—$NR_6R_7$, wherein X is selected from the group of alkylene, arylene or combination thereof from 1 to 18 carbon atoms and the remaining $R_4$, $R_5$, $R_6$ and $R_7$ groups are selected from the group consisting of hydrogen, alkyl and aryl of from, 1 to 18 carbon atoms or combination thereof.

Preferred reaction mixtures for the typical preparation of the composition of this invention have the following oxide molar ratio ranges:

| Reagents | Useful | Preferred |
| --- | --- | --- |
| $K_2O_3/SiO_2$ | 0 to 0.5 | 0.005 to 0.05 |
| $MO_2/SiO_2$ | 0 to 0.2 | 0.01 to 0.1 |
| Hydrolysis agent/$SiO_2$ | 10 to 250 | 20 to 150 |
| Co-solvent/$SiO_2$ | 0 to 150 | 5 to 20 |
| Template/$SiO_2$ | 0.05 to 1 | 0.1 to 0.3 | wherein K is optional and is at least one trivalent element selected from the group consisting of B, Al , Ga, Cr or Fe; M is optional and is at least one tetravalent element different than silicon selected from the group consisting of Ti, V, Ge or Zr; Si is silicon, O is oxygen. One skilled in the art can also substitute Si completely for Ge. The hydrolyzing agent is water, the co-solvent is an organic compound, preferably alcohol, and the template is a non-protonated amine or diamine, preferably primary amine.

The preferred preparation procedures of the said compositions comprise steps as follows:

(i) Preparing silicon or tri- or tetravalent element substituted silicon clear solutions in the presence of co-solvent (optional).

(ii) Aging the silicon solution under stirring for at least 5 minutes at temperature above 0° C.

(iii) Preparing a homogeneous solution of the template in the hydrolyzing agent or co-solvent or a mixture thereof.

(iv) Reacting the clear silicate solution from (i) with the template solution by stirring at a temperature from 0° to 100° C.

(v) Aging the resulting gel under stirring at the desired temperature for at least 30 minutes.

(vi) Air drying and calcinating the product or separating the template by either washing with hot water or ethanol or a mixture thereof, or by distillation of the templated product. After template removal the product is again subjected to calcination to remove trace amounts of template and to complete the crosslinking of the framework.

(vii) Calcining the product at 300° to 1000° C. in air or inert gas for at least 30 minutes, then cooling it off and storing it in hermetic and dry packages.

Herein said silicon or silicon-substituted solutions are prepared from neutral precursors such as alkoxides or silanes, preferably such as alkoxides, in particular, such as aluminum tri-ethoxide, aluminum isopropoxide, aluminum tri- tert- or sec- butoxide, chromium acetate, tetraethyl orthotitanate, tetrapropyl orthotitanate, tetraisopropyl orthotitanate (TIPOT), tetrabutyl orthotitanate, tetraoctadecyl orthotitanate, tetraethyl orthogermanate, tetrapropyl orthozirconite, tetramethyl orthosilicate, tetraethyl orthosilicate (TEOS), tetrapropyl orthosilicate, tetrabuthyl orthosilicate, tetrahexyl orthosilicate, $H(OSi(OC_2H_5)_2)_nOH$ wherein n=4–6, $RSi(OR)_3$ or mixtures thereof.

Said co-solvent is selected from the group of normal or isomerized alcohols having 1 to 12 carbon atoms and at least one OH group, such as methanol, ethanol, propanol, buthanol, hexanol, octanol, dodecanol. More preferably, said co-solvent is an ethanol, propanol, 2-propanol or mixture thereof. Those skilled in the art will know that polyols, such as glycols, in which more than one OH group is present also can be used as a co-solvent. All are classified as "alcohols".

The said aging of the clear solution is preferably performed at 60°–75° C. for 3 to 4 hours for the substituted clear silicon solution.

The said template is a neutral primary, secondary or tertiary amine or polyamine, preferably a primary amine or diamine, more preferably primary amine, having at least one alkyl chain of from 6 to 18 carbon atoms or mixture thereof.

Said reacting of the silicon and template solutions is preferably carried out at 20° to 45° C. by random order of reagent addition, more preferably by adding the silicon solution to the stirred template solution. More specifically said reacting is performed by H-bonding between neutral silicon precursors and a non-protonated template, followed by further hydrolysis and crosslinking of $TO_4$ units at mild reaction conditions. This H-bonding most likely occurs between surface silanol groups (Si—OH) or more generally any T—OH or T-proton donor compound and the lone pair of electrons on the N atom of the organic template.

The said aging of the gel is accomplished preferably for 4 to 24 hours, more preferably from 12 to 18 hours.

Said calcinating is performed by heating in an oven at a temperature preferably from 400°–650° C. for 4 hours.

The outstanding features of the present method are:

(i) The use of non-ionic template, particularly amines or diamines, to assemble the mesoporous framework structure;

(ii) The use of non-ionic precursors such as alkoxides as a source of silicon or the element substituting for silicon;

(iii) The preparation and aging of the clear silicon or substituted silicon solution;

(iv) The aging of the substituted clear silicon solution at 60° to 80° C. for 1 to 4 hours in order to obtain polymerized Si—O—Si, or Si—O—K, or Si—O—M, or mixture thereof species.

(v) The use of hydrogen bonding as a driving force for the assembly process between the neutral amine template and neutral silicon precursor species;

(vi) The use of the new concept of non-ionic amine templating;

(vii) The use of mild reaction conditions to prepare the templated crystalline product;

(viii) The use of new template separation art involving solvent extraction or distillation from the wet product;

(ix) The use of a new inexpensive preparation art.

The silicate compositions of the present invention can be combined with other zeolites or clays or inorganic oxides or organic polymers or mixture thereof, in order to prepare adsorbents, catalysts, catalytic carriers or composite membranes with high thermal and mechanical resistance. In addition, one skilled in the art can impregnate said composition of the present invention or use it as an encapsulating agent for transition metal macrocycles such as phthalocyanines and porphyrins. The active phases in these cases can be transition metals for example Cu, Co, Cr, Ni, Fe, Ti, V, Pt, Pd, Mo, Ir, W and Sn. These catalysts can be used in conversion such as catalytic cracking, hydrocracking, reforming, isomerization, dealkylation or oxidation in the presence or absence of $H_2O_2$ or $O_2$ or mixture thereof.

The following specific examples are intended to be illustrative of the present invention, but are not intended to limit the invention.

EXAMPLES 1–9

The crystalline materials were prepared by a templating mechanism involving H-bonding between neutral primary amine (or diamine), with alkyl chain lengths from $C_6$–$C_{18}$ and neutral silicon alkoxide precursor. In all examples the molar ratio of template to $SiO_2$ was kept constant. Thus, for each experiment the appropriate amount of template (see Table 1) was mixed with 30 ml of deionized $H_2O$ and homogenized by stirring. The pH values of the template solution were found to be in the range of 9.5 to 10.5. 13.66 g of tetraethylorthosilicate (TEOS) were added all at once to each template solution giving a final pH in the range of 9 to 10. The resulting gel was stirred and aged at ambient temperature for 18 hours. Each gel had the following composition in terms of moles per mole $SiO_2$:

0.25 moles $C_nH_{2n+1}NH_2$ (or $C_nH_{2n}N_2H_4$)

24.8 moles $H_2O$

The obtained crystalline products were air-dried at room temperature and calcined at 630° C. for 4 hours in order to remove the incorporated template.

The X-ray diffraction patterns of all samples were measured on a Rigaku Rotaflex diffractometer equipped with rotating anode and Cu-Kα radiation (λ=0.15148 nm). The diffraction data were recorded by step-scanning at 0.01 degrees of 2θ, where θ is the Bragg angle, and counting time of 1 sec per each step. The d-spacings of the X-ray reflections of the samples were calculated in Angstrom units (Å).

The predominant particle sizes and the electron diffraction patterns of all samples were obtained on a JEOL JEM—100 CX II electron microscope by observing microtomed thin sections of the examined material, supported on carbon coated Cu grids (400 mesh). The sample images were obtained using an accelerating voltage of 120 kV, a beam diameter of ≈5 μm and an objective lens aperture of 20 μm. The electron diffraction patterns were recorded by using an accelerating voltage of 100 kV, a beam size of ≈5 μm and a diffraction aperture of 20 μm.

The pore structure of the said samples was characterized by measuring the $N_2$ adsorption-desorption isotherms on a Coulter Omnisorp 360 CX Sorptometer at −195° C. using standard continuous sorption procedures. Before the measurement, each sample was heated overnight at 150° C. and $10^{-6}$ Torr. The specific surface area $S_{BET}$, $m^2/g$) and the total pore volume ($V_t$, cc/g) were calculated from the isotherms following the IUPAC recommendations (Sing et al., Pure Appl. Chem., 57, 603 (1985)). The pore size distribution of the materials was calculated using the method of Horvath and Kawazoe (G. Horvath and K. J. Kawazoe, J. Chem. Eng. Jpn., 16, 470 (1983)). The volume of pores corresponding to framework-confined uniform mesopores was evaluated from the upper inflection point of the low P/Po hysteresis loop and that of the textural mesopores by the formula $V_{textural} = V_{total} - V_{framework-confined}$.

The thermogravimetric analyses of all samples were performed in dry $N_2$ gas on a CAHN system TG analyzer using heating rate of 5° C./min.

The specific amounts of template used in each particular example together with the corresponding X-ray d-spacing of the most intense low angle reflection (100) of the calcined product are summarized in Table 1.

TABLE 1

| Example | Template chain length $C_nH_{2n+1}NH_2$ n = | Amount of template used (g) | X-ray d-spacing (Å) |
| --- | --- | --- | --- |
| 1 | 4 | 1.23 | Amorphous |
| 2 | 6 | 1.7 | 28.5 |
| 3 | 8 | 2.17 | 35.3 |
| 4 | 10 | 2.46 | 28.0 |
| 5 | 12 | 2.92 | 29.0 |
| 6 | 14 | 3.58 | 37.1 |
| 7 | 16 | 4.05 | 39.1 |
| 8 | 18 | 4.52 | 46.5 |
| 9† | $H_2N(CH_2)_{12}NH_2$ | 3.36 | 21.8 |

†1,12-Diaminododecane was used as a template in this example. In addition, 60 ml of $H_2O$ was used for the preparation.

The important trend to notice here is that $d_{100}$ spacing increases proportionally to the template chain length. This is due to the fact that longer alkyl chains afford template micelles with larger diameters. One skilled in the art will know that the $d_{100}$ spacing is directly proportional to the framework-confined mesopore size of the crystalline material. Therefore, the framework-confined mesopore size, i.e. the porosity of our compositions can be tuned in the range of 28.5 to 46.5 Å by careful selection of the alkyl chain length of the template.

EXAMPLES 10-17

These experiments were conducted by a procedure similar to that of Examples 1-9, but in the presence of co-solvent. In each case the co-solvent used was ethyl alcohol (EtOH). The concentration of co-solvent could be varied but for those particular examples it was kept a constant. In contrast to the preparation described in Examples 1-9, the template solution here was obtained in a different manner. Thus, the template solutions of these examples were prepared by mixing and homogenizing of the corresponding amount of template, given in Table 1, with 35 ml of $H_2O$ and 35 ml of EtOH under stirring. The addition of co-solvent to the templated solutions of these examples did not give any change in the measured pH values (9.5 to 10.5). Each gel mixture here had a molar composition as expressed per mole of $SiO_2$:

0.25 moles $C_nH_{2n+1}NH_2$ (or $C_nH_{2n}H_2H_4$)
28.94 moles $H_2O$
8.94 moles EtOH The corresponding X-ray d-spacings of the calcined products are listed in Table 2.

TABLE 2

| Example | Template chain length $C_nH_{2n+1}NH_2$ n = | X-ray d-spacing (Å) |
| --- | --- | --- |
| 10 | 6 | Amorphous |
| 11 | 8 | 35.9 |
| 12 | 10 | 33.7 |
| 13 | 12 | 35.3 |
| 14 | 14 | 43.0 |
| 15 | 16 | 48.0 |
| 16 | 18 | 42.1 |
| 17† | $H_2N(CH_2)_{12}NH_2$ | 23.4 |

†1,12-Diaminododecane was used as a template in this example. In addition 60 ml of $H_2O$ was used in this preparation instead of 30 ml.

The comparison of the above d100 values with those in Table 1 reveals similar trend of d-spacings increase. Thus, the framework-confined mesopore size, i.e. the porosity of the compositions, prepared in the presence of co-solvent can be tuned in the range of 35.9 to 48.0 Å. An interesting trend is observed from the $N_2$ adsorption-desorption isotherms of the products of these Examples. Apparently, the longer the template alkyl chain the smaller the textural to framework-confined mesoporosity ratio. Thus, the variation in the ratio was found to be from 5 to 0.2. This implies that the ratio of textural to framework-confined mesoporosity in the compositions of the present invention can be tuned by careful selection of the template chain length. This teaching is not apparent from the prior art synthetic methods (U.S. Pat. Nos. 5,098,684, 5,102,643 and 5,057,296).

EXAMPLE 18

The following example was conducted in order to demonstrate the preparation of a Ti-substituted crystalline silicate material having complementary framework-confined uniform mesopores and textural mesopores. These materials can be used as adsorbents and catalysts for the conversion of large organic substrates. For this particular experiment 13.66 g of TEOS were added to 25 ml of EtOH and stirred. A solution of 0.225 g tetraisopropyl orthotitanate (TIPOT) in 10 ml isopropyl alcohol (i-PrOH) was quickly added to the TEOS solution under vigorous stirring. The resulting clear mixture was then heated and stirred at 65°–75° C. for 3 hours to obtain the —Ti—O—Si— polymerized species.

Figure 2:
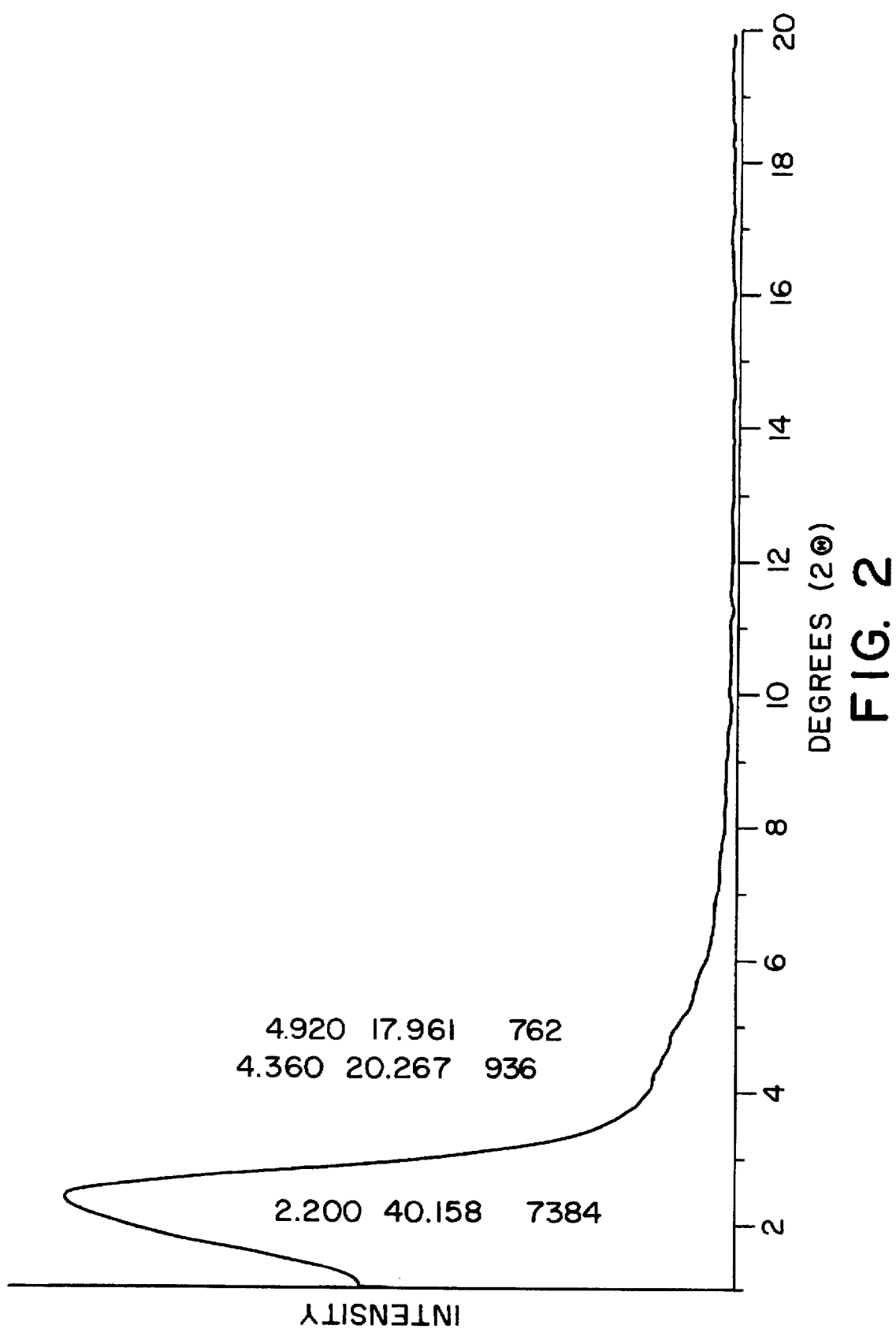
FIG. 2 is an X-ray diffraction pattern of the product of Example 18.
Figure 3:
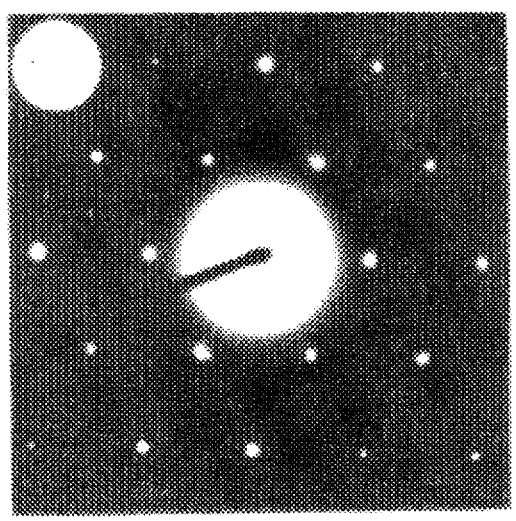
FIG. 3 is an electron diffraction pattern of the product of Example 18.
Figure 4:
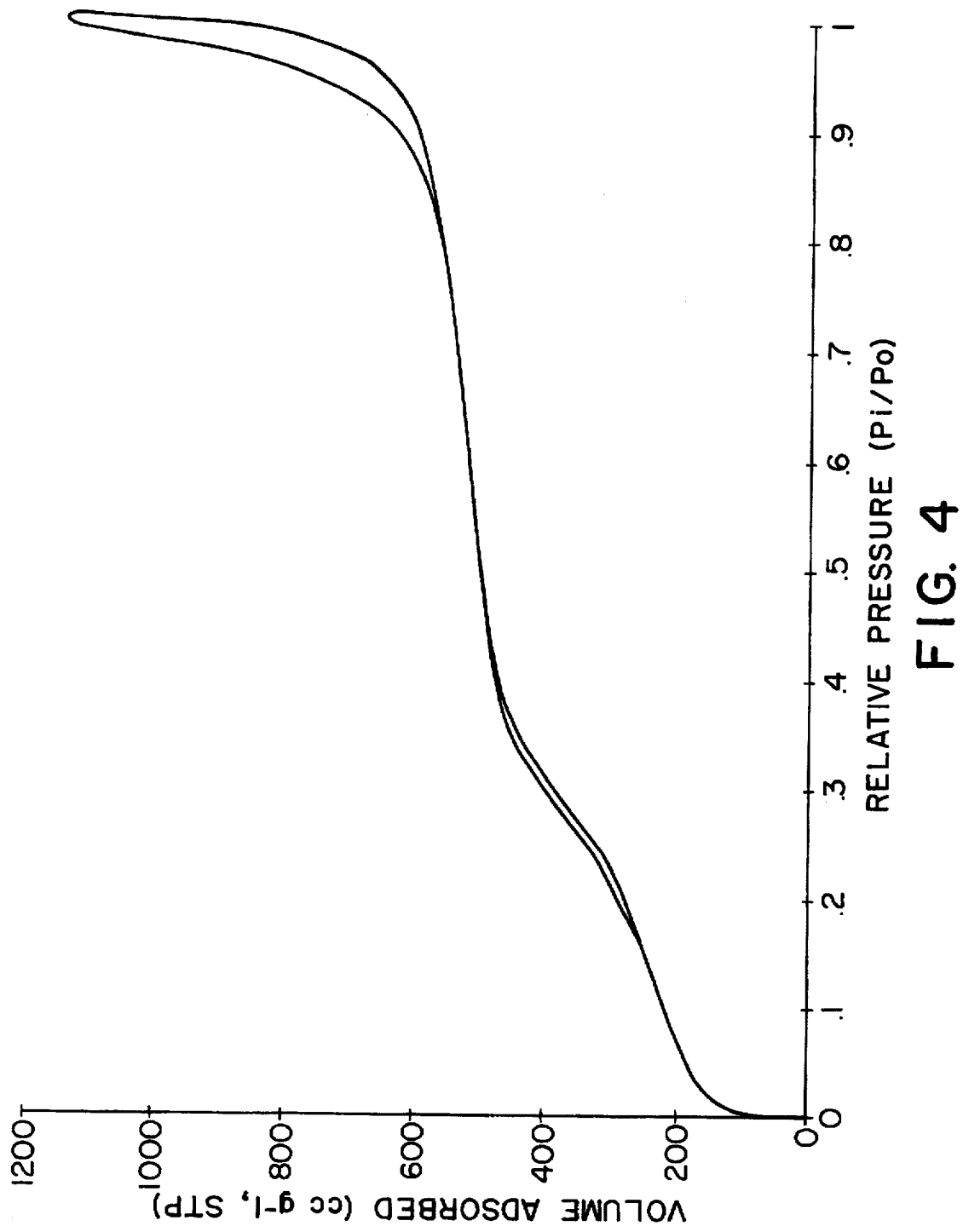
FIG. 4 is a N₂ adsorption-desorption isotherm of the product of Example 18.
Figure 5:
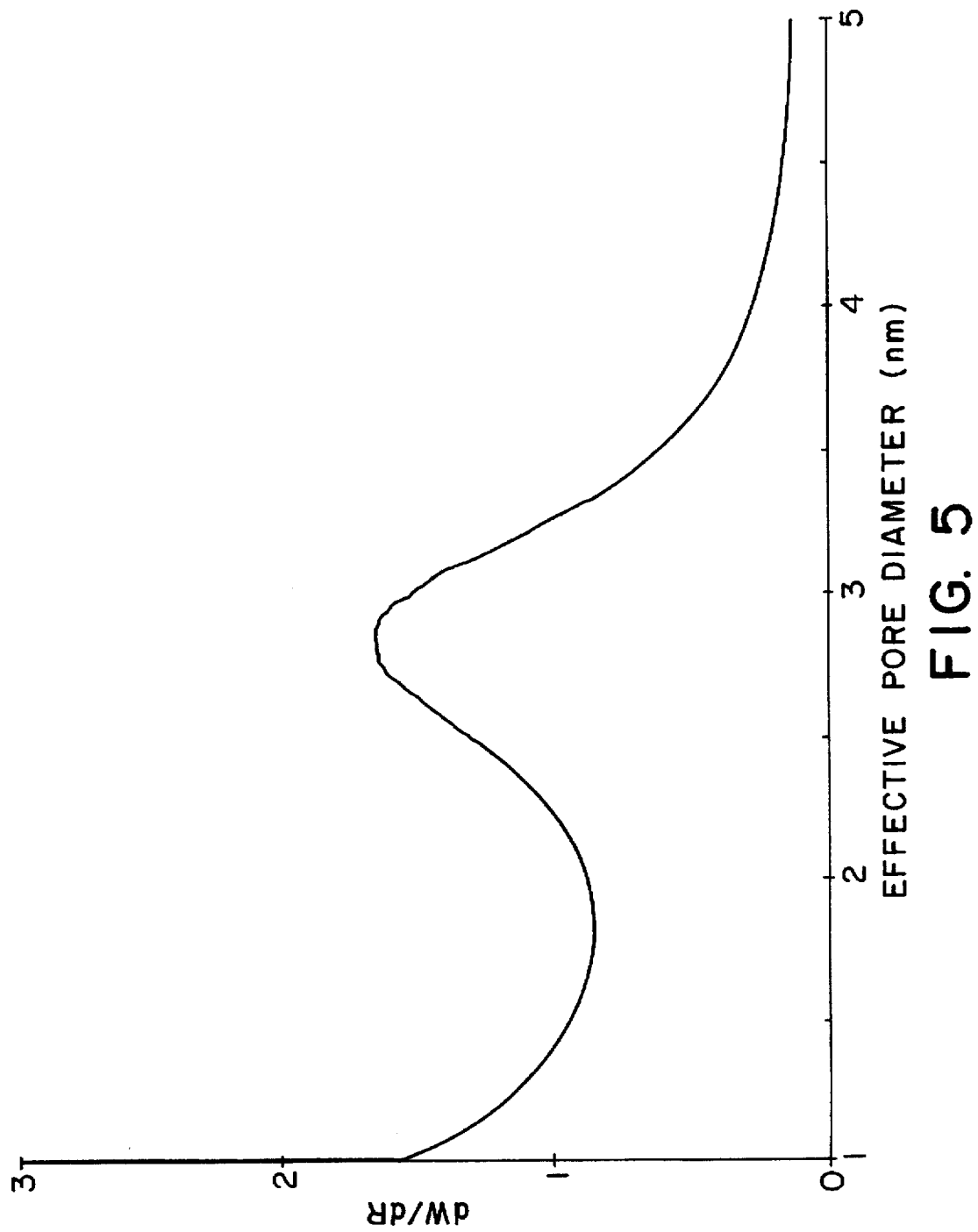
FIG. 5 is a Horvath-Kawazoe pore size distribution of the product of Example 18.

A separate solution of 3.27 g of dodecylamine (DDA) in 25 ml of water was prepared under stirring. The clear Ti—O—Si solution was aged and then added at once to the above template solution. The resulting mixture was stirred and aged at ambient temperature for 16 hours in order to prepare the said crystalline product. The molar composition of the gel per mole of $SiO_2$ was:

0.01 moles $TiO_2$
0.27 $C_nH_{2n+1}NH_2$
20.67 moles $H_2O$
6.54 moles EtOH
1.95 moles of i-PrOH The product was air dried and calcined at 650° C. for 4 hours. The X-ray diffraction pattern of the calcined product of this example is shown in FIG. 2. It exhibits a strong relative intensity peak at 40.2±1.0 Å d- spacing and a diffuse scattering centered at ≈18.0±2.0 Å. The particle size of the product was found to be <250 Å. The electron diffraction pattern of this product, presented as FIG. 3, shows typical hexagonal arrangement of the diffraction maxima similar to that observed for MCM-41 type materials by prior art (U.S. Pat. No. 5,098,684). The $N_2$ adsorption—desorption isotherm of this product, shown in FIG. 4 is composed by two well-defined hysteresis loops corresponding to the presence of complementary framework-confined and textural mesoporosity. The $S_{BET}$ of the crystalline product of this example is 1046 m²/g and the $V_t$—1.75 cc/g. The pore volume corresponding to the uniform framework mesopores is 0.71 cc/g and the volume of textural mesopores is 1.04 cc/g. The ratio of textural to framework mesoporosity here is 1.46. The size of framework-confined uniform pores of the product as determined from Horvath-Kawazoe pore size distribution curve is 28 Å (FIG. 5).

EXAMPLE 19

The following experiment exemplifies the new template recovery of the present invention.

Figure 6:
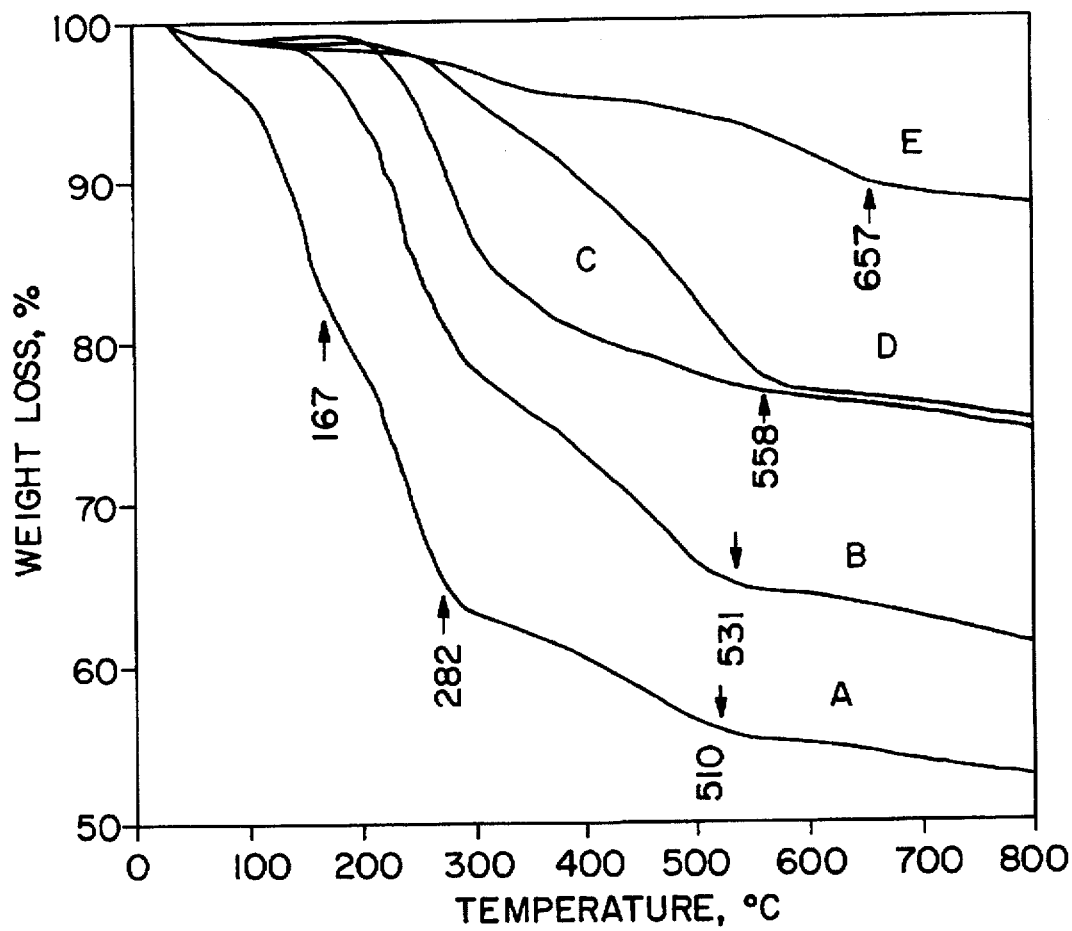
FIG. 6 is thermogravimetric curves of the product of Examples 19 (A); 20 (B); 21 (C); 22 (D) and 23 (E).

(Product A) A 0.03 g of the air dried and non-calcined product of Example 18 was subjected to thermogravimetric analysis (TGA) in $N_2$ gas flow at heating rate 5° C./min. The corresponding weight loss curve is shown in FIG. 6A. The total weight loss of this sample is ≈46%. This curve is constituted of three distinguishable weight loss steps at the ranges of 167°, 282° and 510° C. which could be attributed to the loss of adsorbed water, decomposition or desorption of template and dehydroxylation of the surface, respectively.

(Product B) One gram of the air dried and non-calcined product of Example 18 was mixed with 150 ml deionized water and stirred. The mixture was then heated at 75° C. for 30 minutes in order to intensify the template removal. The product was filtered and washed with another portion of deionized water (150 ml). The above washing procedure was repeated two more times and the filtrated product was air dried at a temperature of 80° C. to remove the bulk water. The TGA curve of this product is presented in FIG. 6B. The total weight loss for this sample is approximately 37%. The X-ray diffraction pattern of the washed and dried product of this example exhibits one strong reflection at $d_{100}$=47.5±1 Å.

(Product C) A 0.278 g of the air dried product of Example 18 were placed in a standard glass sample bulb of Culter Omnisorp 360 CX Sorptometer, attached to the outgasing section of the instrument heated at 150° C. to vacuum distill the template until a residual pressure of $10^{-4}$ Torr was reached. The TGA curve of the distillated product is shown in FIG. 6C. The total weight loss here is 20%. The X-ray diffraction pattern of the product, subjected to vacuum distillation, shows strong $d_{100}$ reflection at 47.5±1 Å and diffuse scattering at 22.0±2 Å.

(Product D) A 0.189 g of the air dried Product B were placed in a standard glass sample bulb of Coulter Omnisorp 360 CX sorptometer and subjected to vacuum outgasing at 150° C. as described above. The TGA curve of the product of this example is presented in FIG. 6D. In contrast to the previous examples the total TG weight loss here is ≈23%. The X-ray diffraction pattern of the vacuum distilled product of this example exhibits single broad $d_{100}$ reflection at 67.0±1 Å.

Figure 7:
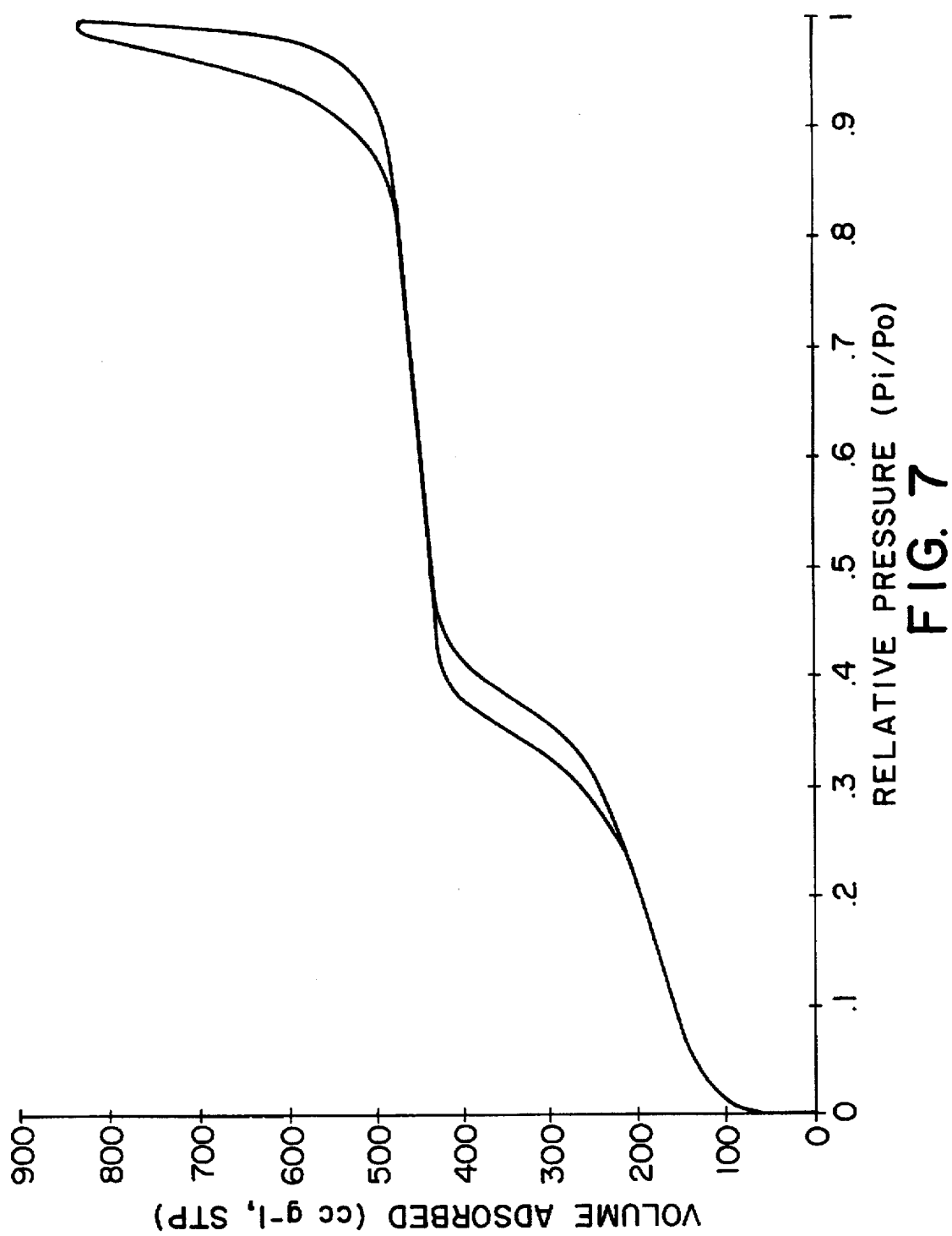
FIG. 7 is a graph showing N₂ adsorption-desorption isotherm of the product E of Example 19.
Figure 8:
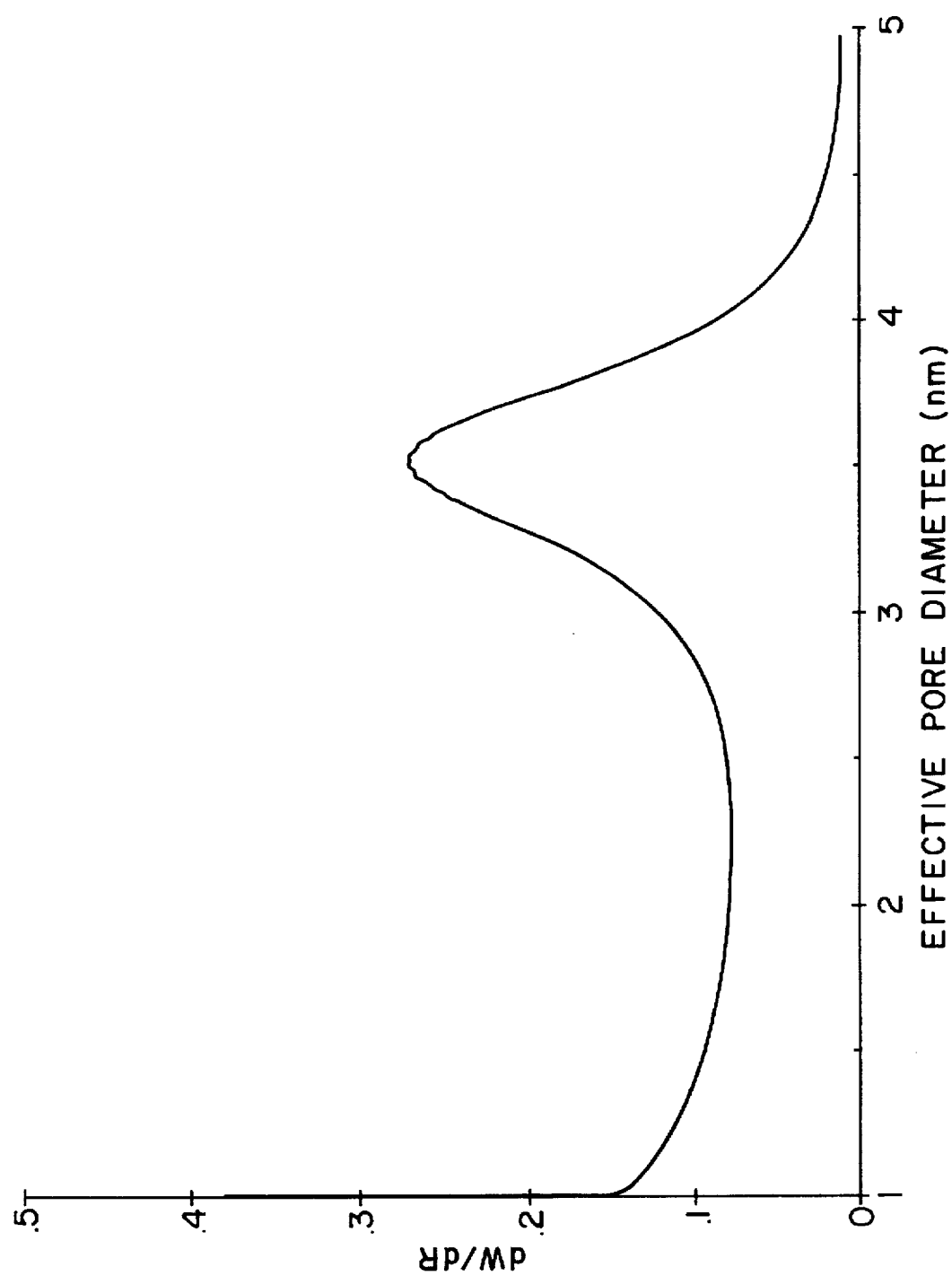
FIG. 8 is a graph showing Horvath-Kawazoe pore size distribution of the product E of Example 19.

(Product E) One gram of the air dried and non-calcined product of Example 18 was mixed with 100 ml of EtOH, stirred and heated, preferably in the range of 45° to 72° C. for 30 minutes. The product was then filtered and washed with another portion of EtOH (100 ml). The above washing procedure was repeated twice and the filtrated product was air dried at 80° C. The product was subjected to TGA analysis and the obtained curve is presented in FIG. 6E. The total weight loss of this product is only 11%, with approximately 9% due to loss of water and less than 2% due to loss of residual template. The absence of amine was also confirmed by the absence of C—H stretching bands on the IR spectrum of the product. Surprisingly, the X-ray diffraction pattern of the EtOH washed product exhibits four times stronger $d_{100}$ reflection at 47.6±1 Å than the products of Examples 18 to 22. In addition, a well-expressed diffuse scattering at 22.3±2 Å is also observed. The $N_2$ adsorption-desorption isotherm and the Horvath-Kawazoe pore size distribution of this product, shown in FIGS. 7 and 8 respectively, and the corresponding textural to framework-confined mesoporosity ratio (0.91) are very similar to those of the calcined product (see Example 18). This implies that the neutral template has been efficiently removed from the framework of our compositions by ethanol extraction. The extracted organic template in the form of EtOH solution can be recycled and reused after simple concentration of the solution.

EXAMPLE 20

The preparation procedure employed here was identical to that of Example 18 except that the order of addition of solutions was changed. In contrast to this previous example the template here was mixed first with the Ti-silicon solution under vigorous stirring. The corresponding amount of water was then added at once to the above clear template/Ti-silicon solution. The calcined product exhibits X-ray d-spacing of 42.5±2.0 Å and diffuse scattering at 18.0±2.0 Å. The particle size of the product, as judged by TEM, was found to be <300 Å. The $SEB_T$ of the product is 968 m²/g and the $V_t$ is 1.82 cc/g. The pore volume corresponding to the uniform framework-confined mesopores is 0.45 cc/g and the volume of textural mesopores was 1.37 cc/g. The textural to framework-confined mesoporosity ratio for this sample was found to be 3.12. The pore size of the product as determined by Horvath-Kawazoe method is 27 Å.

EXAMPLE 21

Figure 9:
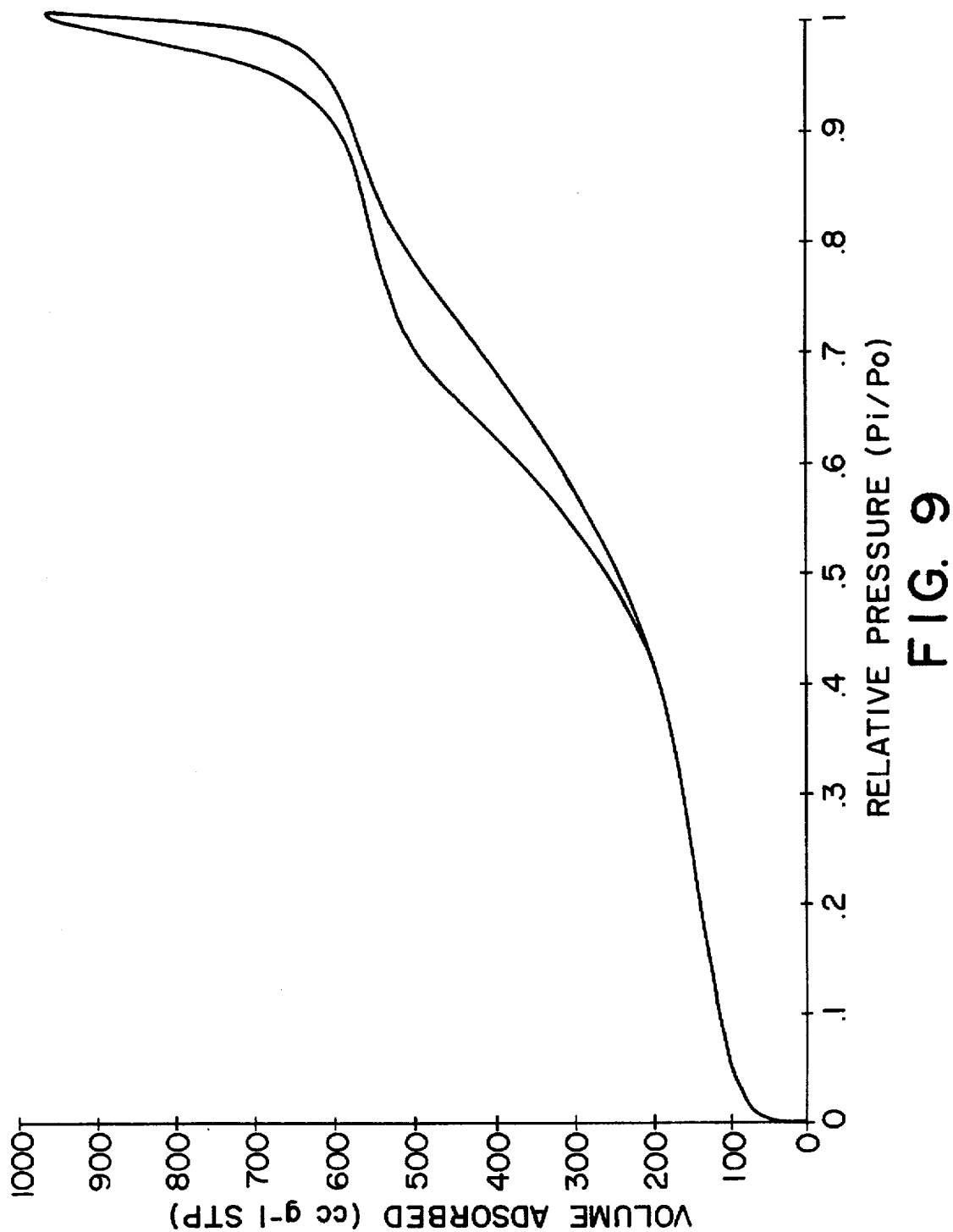
FIG. 9 is a graph showing N₂ adsorption-desorption isotherm of the product of Example 21.

A 27.32 g of TEOS in 50 ml of EtOH were added slowly to a solution of 0.45 g of TIPOT in 25 ml of i-PrOH. The resulting clear solution was stirred and heated at 65°–70° C. for 4 hours. A separate solution of 6.54 g DDA (template) in 90 ml of $H_2O$ was prepared and homogenized for 30 minutes. The aged Ti—O—Si solution was added at once to the template (DDA) solution and the obtained gel was stirred at ambient temperature for 30 minutes. The molar composition of the gel as expressed per mole of $SiO_2$ was:

0.01 moles $TiO_2$ 0.27 moles $C_nH_{2n+1}NH_2$ 74.4 moles $H_2O$ 6.4 moles EtOH 1.25 moles of i-PrOH The gel was loaded in 1000 cc autoclave, stirred and allowed to react at 100° C. for 12 hours. The calcined product was the mesoporous material of the present invention, having an X-ray pattern similar to that of the product of Example 18, and a d-spacing of 71.2±2.0 Å. The particle size of this product, as judged by TEM, was found to be ≈400 Å. The $S_{BET}$ of the product was 527 m²/g and the $V_t$ was 1.53 cc/g. The $N_2$ adsorption isotherm of this crystalline product is shown in FIG. 9. In contrast to previous art materials, and the material of this invention prepared according to the Examples 1–18 and 24, this product exhibits much larger framework-confined uniform mesopore size. This is evidenced by the slope and location of the first hysteresis loop of the $N_2$ adsorption-desorption isotherm versus Pi/Po axis (See FIG. 7). The corresponding Horvath-Kawazoe pore size distribution of this product was found to be ≈50 Å. It is speculated that the presence of alcohol in the gel, as well as the hydrothermal conditions applied are responsible for the formation of large template micelles, i.e. large framework-confined mesopore size. In contrast to the previous art, as described in U.S. Pat. No. 5,057,296, which used an expensive auxiliary organic to expand the pore size of MCM-41 type materials, the framework-confined uniform mesopore size of our composition was expanded without using a special organic pore expanding agent. This was accomplished by a relatively short hydrothermal treatment of the final gel in the presence of a co-solvent (EtOH). The ratio of framework to textural mesoporosity here is 0.8.

EXAMPLE 22

The catalytic activity of Ti-framework substituted materials of the present invention in catalytic peroxide oxidation of aromatic compounds is set forth in this example. The final product of Example 18 was chosen for this purpose and subjected to evaluation for the oxidation of phenol to the corresponding quinone. The catalytic experiment was conducted at temperature of 62° C. for 2 hours using 100 mg of catalyst, 10 mmoles of phenol as a substrate, 0.13 moles of acetone as a solvent and 29 mmol of 30% $H_2O_2$. The material of this invention was found to give phenol conversion of 77% with >90% selectivity toward the corresponding quinone. It should be noted that a comparative run with the non-substituted material (non Ti) of this invention (Example 13) did not give any significant conversion due to the lack of active sites.

Certain aspects of the present invention are disclosed by the inventors and one other person in Nature, 368, 321–323 (March 1994). This publication is incorporated by reference herein.

It is intended that the foregoing description be only illustrative of the present invention and that the present invention be limited only by the hereinafter appended claims.

We claim:

1. A calcined crystalline silicate containing composition having uniform framework-confined mesopores having a pore size greater than about 20 Å as determined by $N_2$ adsorption and textural mesopores and consisting essentially of particles with a size of less than about 400 Å, two hysteresis loops in a $N_2$ adsorption-desorption isotherm, a ratio of textural to framework mesopores of at least about 0.2, a specific surface area of 300 to 1500 square meters per gram, prepared by a method which comprises reacting a neutral silicon-containing inorganic oxide precursor, a Ti containing inorganic oxide precursor and a neutral amine template in water and an organic co-solvent to form a reaction product and hydrolysis of the reaction product and has a composition as follows:

$$L_xM_ySi_zO_q$$

wherein L is optional and is at least one trivalent element selected from the group consisting of B, Al, Ga, Cr and Fe; M is Ti; x, y, z and q are the molar parts of L, M, Si and O, respectively and wherein x when L is present is about 0.001 and 0.5; y is between about 0.001 and 0.4; z is between about 0.4 and 1 and q is between about 1 and 3.

2. The composition of claim 1 wherein L is Al.

3. The composition of claim 2 wherein y is between about 0.005 and 0.25.

4. The composition of claim 3 wherein q is 2.

5. The composition of claim 4 having an X-ray diffraction pattern as shown in FIG. 2.

6. The composition of claim 5 having an electron diffraction pattern as shown in FIG. 3.

7. The composition of claim 6 having a $N_2$ adsorption-desorption isotherms as shown in any one of FIGS. 4, 7 and 9 and a Horvath-Kawazoe pore size distribution as shown in any one of FIGS. 5 and 8.

8. A composite material prepared from the composition of claim 1 admixed with materials selected from the group consisting of aluminas, clays, zeolites, polymers and mixtures thereof.

9. The composition of claim 1 containing at least one metal selected from the group consisting of Cu, Co, Cr, Ni, Fe, Ti, V, Mo, Pt, Pd, Ir, W and Sn in the mesopores.

10. The composition of claim 1 which is $Ti_ySi_zO_q$.

11. A method for preparation of a synthetic, crystalline silicate composition which can be calcined comprising:

(a) preparing an aged, non-ionic silicon precursor solution containing an organic co-solvent with stirring at a temperature of at least 0° C. for at least 5 minutes wherein the solution can optionally contain a metal as an inorganic oxide precursor;

(b) preparing a homogeneous solution of a non-ionic amine template in a hydrolysis agent selected from the group consisting of water, the organic co-solvent and mixtures thereof with stirring at a temperature between about 0° and 100° C.;

(c) mixing of the solutions of steps (a) and (b) at a temperature between about 0° and 100° C. to form a gel which is aged for at least thirty minutes to form a crystalline product; and (d) separating the template and at least some of the hydrolysis agent from the crystalline product, wherein the template produces a pore size of greater than 20 Å in the silicate composition.

12. The method of claim 11 wherein said crystalline material in a calcined and anhydrous state has a composition as follows:

wherein L is optional and is at least one element selected from the group consisting of B, Al, Ga, Cr and Fe; M is selected from the group consisting of Ti, V, Ge and Zr; x, y, z and q are the molar parts of L, M, Si and O, respectively and wherein x when L is present is for a total of L between 0.001 and 0.5; y when M is present is for a total of M between 0.001 and 0.4; z is between 0.4 and 1 and q is between about 1 and 3.

13. The method of claim 11 wherein said template is a neutral amine of formula $R_1R_2R_3N$, wherein N is nitrogen and at least one of $R_1$, $R_2$ and $R_3N$ is selected from the group consisting of alkyl of from 6 to 18 carbon atoms, aryl of from 6 to 18 carbon atoms and and the remaining of $R_1$, $R_2$ and $R_3$ are selected from the group consisting of hydrogen and alkyl containing 1 to 18 carbon atoms.

14. The method of claim 11 wherein said template is a neutral diamine of formula $R_4R_5NXNR_6R_7$ wherein X is selected from the group consisting of alkylene, arylene and mixtures thereof containing from 1 to 18 carbon atoms and $R_4$, $R_5$, $R_6$ and $R_7$ are selected from the group consisting of hydrogen, alkyl of from 1 to 18 carbon atoms and aryl of from 6 to 18 carbon atoms.

15. The method of claim 11 wherein said silicon precursor containing solution in step (a) contains an alkoxide.

16. The method of claim 12 wherein said trivalent element is Al.

17. The method of claim 12 wherein said element M is selected from the group consisting of Ti and V.

18. The method of claim 11 wherein the template homogenous solution is added to th silicon containing precursor aqueous solution.

19. The method of claim 11 wherein in step (a) the non-ionic silicon-containing solution is prepared from a material selected from the group consisting of tetraethylorthosilicate (TEOS); a mixture of TEOS and aluminum-tri-sec-butoxide, and a mixture of TEOS and tetraisopropyl orthotitanate.

20. The method of claim 11 wherein the template is separated by extraction of the crystalline product in step (d) with a solution comprising a solvent for the template.

21. The method of claim 11 wherein the crystalline product without the template is produced by being subjected to air drying and then calcination at 600° to 650° C. in a gas atmosphere for about 4 hours.

22. The method of claim 12 wherein the silicate containing composition is prepared with $L_2O_3$ in a mole ratio between about 0.005 and 0.05 mole per mole $SiO_2$ and wherein M as a metal oxide is present in a mole ratio between 0.01 and 0.2 mole per mole $SiO_2$.

23. The method of claim 20 wherein the hydrolysis agent is water admixed with ethyl alcohol as the organic co-solvent and wherein the water is between about 20 to 150 moles per mole $SiO_2$ and the ethyl alcohol is between about 5 and 20 moles per mole $SiO_2$.

* * * * *

UNITED STATES PATENT AND TRADEMARK OFFICE
CERTIFICATE OF CORRECTION

PATENT NO. : 5,672,556
DATED : September 30, 1997
INVENTOR(S) : Thomas J. Pinnavaia and Peter T. Tanev It is certified that error appears in the above-identified patent and that said Letters Patent is hereby corrected as shown below:

Column 1, line 35, "pore 30 volume" should be --pore volume--.

Column 2, line 33, "by $Al_{3+}$" should be --by $Al^{3+}$--.

Column 5, line 12, "$(S^+X^{31}I^+)$ where $X^{31}=Cl^{31}$, $Br^{31}$" should be --$(S^+X^-I^+)$ where $X^-=Cl^-, Br^-$ --.

Column 6, line 62, "of size >2m" should be --of size >2 $\mu$m--.

Column 7, line 36, "assess" should be --access--.

Column 12, line 20, "groups of $R_1$, and $R_3$" should be --groups of $R_1$, $R_2$ and $R_3$--.

Column 13, line 18, "tetrabuthyl" should be --tetrabutyl- --.

Column 18, line 30, "$SEB_T$" should be --$S_{BET}$--.

UNITED STATES PATENT AND TRADEMARK OFFICE
CERTIFICATE OF CORRECTION

PATENT NO. : 5,672,556
DATED : September 30, 1997
INVENTOR(S) : Thomas J. Pinnavaia and Peter T. Tanev It is certified that error appears in the above-identified patent and that said Letters Patent is hereby corrected as shown below:

Column 20, line 54 (Claim 13) "$R_1$, $R_2$ and $R_3N$" should be --$R_1$, $R_2$ and $R_3$--.

Column 20, line 56 (Claim 13), "and", second occurrence, should be deleted.

Column 21, line 6, "th" should be --the--.

Signed and Sealed this

Seventeenth Day of March, 1998

*Attest:*

BRUCE LEHMAN

*Attesting Officer*  Commissioner of Patents and Trademarks